(12) United States Patent
Neta

(10) Patent No.: US 7,839,428 B2
(45) Date of Patent: Nov. 23, 2010

(54) SPECTRAL BAND SEPARATION (SBS) MODULES, AND COLOR CAMERA MODULES WITH NON-OVERLAP SPECTRAL BAND COLOR FILTER ARRAYS (CFAS)

(76) Inventor: Uri Neta, Koranit, 20181 Koranit (IL)

( * ) Notice: Subject to any disclaimer, the term of this patent is extended or adjusted under 35 U.S.C. 154(b) by 486 days.

(21) Appl. No.: 11/883,178

(22) PCT Filed: Jan. 29, 2006

(86) PCT No.: PCT/IL2006/000116

§ 371 (c)(1), (2), (4) Date: Jul. 27, 2007

(87) PCT Pub. No.: WO2006/080018

PCT Pub. Date: Aug. 3, 2006

(65) Prior Publication Data

US 2008/0309797 A1 Dec. 18, 2008

(30) Foreign Application Priority Data

Jan. 31, 2005 (IL) .................................... 166595

(51) Int. Cl.
- H04N 13/00 (2006.01)
- H04N 9/07 (2006.01)
- A62B 1/04 (2006.01)
- A61C 1/00 (2006.01)
- A61C 3/00 (2006.01)

(52) U.S. Cl. ............................. 348/45; 348/65; 348/66; 348/338; 433/29

(58) Field of Classification Search .............. 348/36–39, 348/49, 85, 143–160, 218.1, 338, 65–76, 348/42, 45, 46, 339; 396/17; 433/25, 29–31; 359/462

See application file for complete search history.

(56) References Cited

U.S. PATENT DOCUMENTS 4,167,756 A * 9/1979 Smith ........................ 348/343

(Continued)

FOREIGN PATENT DOCUMENTS

GB 670615 1/2006

(Continued)

OTHER PUBLICATIONS

Supplementary European Search Report (SESR) issued on Apr. 27, 2009, in the corresponding foreign patent application No. EP 06 701 520.6, published on Oct. 31, 2007 as EP 1849294.

*Primary Examiner*—David L Ometz
*Assistant Examiner*—Richard Bemben
(74) *Attorney, Agent, or Firm*—Abraham Hershkovitz; Harold L. Novick; Hershkovitz & Associates, LLC

(57) ABSTRACT

Spectral Band Separation (SBS) modules including at least one dichroic element for imaging at least two different still or video images along non co-directional lines of sight for imaging purposes including inter alia displaying multiple 2D images, displaying Extended Field Of View (EFOV) images, stereoscopic imaging, 3D image rendering, and the like. The SBS modules can be implemented as discrete optical attachments for mounting on a color camera module or alternatively can be integrally formed therewith.

13 Claims, 14 Drawing Sheets

U.S. PATENT DOCUMENTS

| | | | |
|---|---|---|---|
| 4,288,819 A * | 9/1981 | Williams | 348/343 |
| 4,846,154 A | 7/1989 | MacAnally et al. | |
| 4,853,764 A * | 8/1989 | Sutter | 348/53 |
| 4,885,634 A * | 12/1989 | Yabe | 348/71 |
| 5,124,547 A * | 6/1992 | Melman | 250/226 |
| 5,434,704 A * | 7/1995 | Connors et al. | 359/403 |
| 5,547,369 A | 8/1996 | Sohma et al. | 431/75 |
| 5,708,470 A * | 1/1998 | Holford | 348/61 |
| 5,727,242 A | 3/1998 | Lo et al. | |
| 5,756,988 A * | 5/1998 | Furuta | 250/208.1 |
| 5,790,185 A * | 8/1998 | Auzerais et al. | 348/84 |
| 5,880,781 A | 3/1999 | Udagawa et al. | |
| 5,883,662 A | 3/1999 | Zanen | |
| 5,940,126 A * | 8/1999 | Kimura | 348/294 |
| 5,975,710 A * | 11/1999 | Luster | 359/856 |
| 6,122,100 A * | 9/2000 | Miller | 359/402 |
| 6,293,911 B1 | 9/2001 | Imaizumi et al. | |
| 6,507,747 B1 | 1/2003 | Gowda et al. | |
| 6,561,972 B2 * | 5/2003 | Ooshima et al. | 600/173 |
| 6,603,876 B1 | 8/2003 | Matsuo et al. | |
| 6,678,398 B2 * | 1/2004 | Wolters et al. | 382/128 |
| 6,704,043 B2 | 3/2004 | Goldstein et al. | |
| 6,721,500 B2 * | 4/2004 | Perisic | 396/331 |
| 7,179,222 B2 * | 2/2007 | Imaizumi et al. | 600/109 |
| 7,553,276 B2 * | 6/2009 | Iddan | 600/160 |
| 2004/0220464 A1 * | 11/2004 | Benninger et al. | 600/407 |
| 2004/0263612 A1 * | 12/2004 | Harter et al. | 348/49 |

FOREIGN PATENT DOCUMENTS

| | | | |
|---|---|---|---|
| JP | 2002-290788 | * | 10/2002 |
| WO | WO 2006/080018 A3 | | 3/2006 |

* cited by examiner

|  | DE29 | | DE37 | | DE38 | |
| --- | --- | --- | --- | --- | --- | --- |
|  | R1 | T1 | R2 | T2 | R3 | T3 |
| RGBE CFA | 400-460 | 480-700 | 480-530 | 540-700 | 540-590 | 600-700 |
| 4C NOSB CFA | 400-475 | 476-700 | 476-550 | 551-700 | 551-625 | 626-700 |

SPECTRAL BAND SEPARATION (SBS) MODULES, AND COLOR CAMERA MODULES WITH NON-OVERLAP SPECTRAL BAND COLOR FILTER ARRAYS (CFAS)

CROSS-REFERENCE TO RELATED APPLICATIONS

This application is the U.S. National Phase filing of PCT Application PCT/IL2005/000116 filed Jan. 29, 2006, the contents of which are incorporated in its entirety herein by reference.

FIELD OF THE INVENTION

The invention is in the field of 2D and 3D imaging applications.

BACKGROUND OF THE INVENTION

Color camera modules include imaging optics with an optical axis, an image sensor with a Color Filter Array (CFA), and an output interface with analog and/or digital outputs for transmitting still or live video signals for display purposes. Various formats of CFAs are now available including the original Bayer format, the more recent RGBE format, and the like. Bayer CFAs filter incoming visual light into three overlapping spectral bands R 550-700 nm, G 475-600 nm, and B 400-550 nm for matching human color perception (see FIG. 1). RGBE CFAs filter incoming visual light into four overlapping spectral bands for better matching human color perception than Bayer CFAs (see FIG. 2). CFAs are available in different tessellations based on different regular polygons such as squares, hexagons, and the like. Analog outputs include inter alia video composite, RGB, and the like. Digital outputs include inter alia USB2, FireWire, CameraLink, Low Voltage Differential Signaling (LVDS), and the like. An exemplary analog color camera module is Model No. CV-M8 CL Color Camera available from JAI Pulnix, Inc. USA. An exemplary digital color camera module is OV7620 Single Chip CMOS VGA Color Digital Camera available from OmniVision Technologies, Inc., 930 Thompson Place, Sunnyvale, Calif. 94085 USA (www.ovt.com).

3D imaging requires a pair of images of the same object along two non co-directional lines of sight. GB 670,615 entitled Improvements in or relating to Apparatus for Taking Stereoscopic Pictures without Abnormal Stereoscopic Effects, U.S. Pat. No. 5,727,242 to Lo et al., U.S. Pat. No. 5,883,662 to Zanen, U.S. Pat. No. 6,603,876 to Matsuo et al., U.S. Pat. No. 6,721,500 to Perisic et al., employ mirror based optical configurations for achieving same. U.S. Pat. No. 6,704,043 to Goldstein et al. employs a lenticular lens array similar to an insect eye in which each lens lies over a single pixel for achieving same.

SUMMARY OF THE INVENTION

The first aspect of the present invention is for Spectral Band Separation (SBS) modules each including at least one dichroic element for imaging at least two different still or video images along non co-directional lines of sight on an image sensor. SBS modules can be designed to be operative in the 400-700 nm visual spectral band only, or the >700 nm IR spectral band only, or the <400 nm UV spectral band only, or a combination of same. SBS modules can be implemented as adapters for interchangeable mounting on camera modules in a similar manner to still cameras with an interchangeable lens system including a zoom lens, a wide angle lens, and the like, or as application specific image acquisition systems including fixed SBS modules.

The second aspect of the present invention is directed toward color camera modules with image sensors having CFAs designed to filter incoming radiation into non-overlapping spectral bands for affording better image separation than conventional CFAs. The spectral bands can be of equal or different bandwidths, and within the 400-700 nm visual spectral band only, or the >700 nm IR spectral band only, or the <400 nm UV spectral band only, or a combination of same. Color camera modules with image sensors having CFAs in accordance with the second aspect of the present invention can have analog and/or digital output interfaces similar to their commercially available counterparts, and their CFAs can have different tessellations similar to conventional CFAs.

The present invention is suitable for a wide range of 2D and 3D imaging applications in the field of surveillance, medical imaging, machine vision inspection, and the like. 2D imaging applications include inter alia displaying multiple 2D images, combining two or more images for displaying Extended Field Of View (EFOV) images, and the like. Depending on the number of 2D images being combined, EFOV images can lie on an optical plane including an imaging optic's optical axis, an optical plane inclined to an imaging optic's optical axis, or a combination of same. Particular 2D imaging applications include inter alia endoscopes and particularly capsule endoscopes, and the like. Capsule endoscopes are available under the commercial name PillCam™ Capsules from Given Imaging Ltd, Yoqneam, Israel. 3D imaging applications include stereoscopic imaging, 3D image rendering, and the like.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE PRESENT INVENTION

Figure 1:
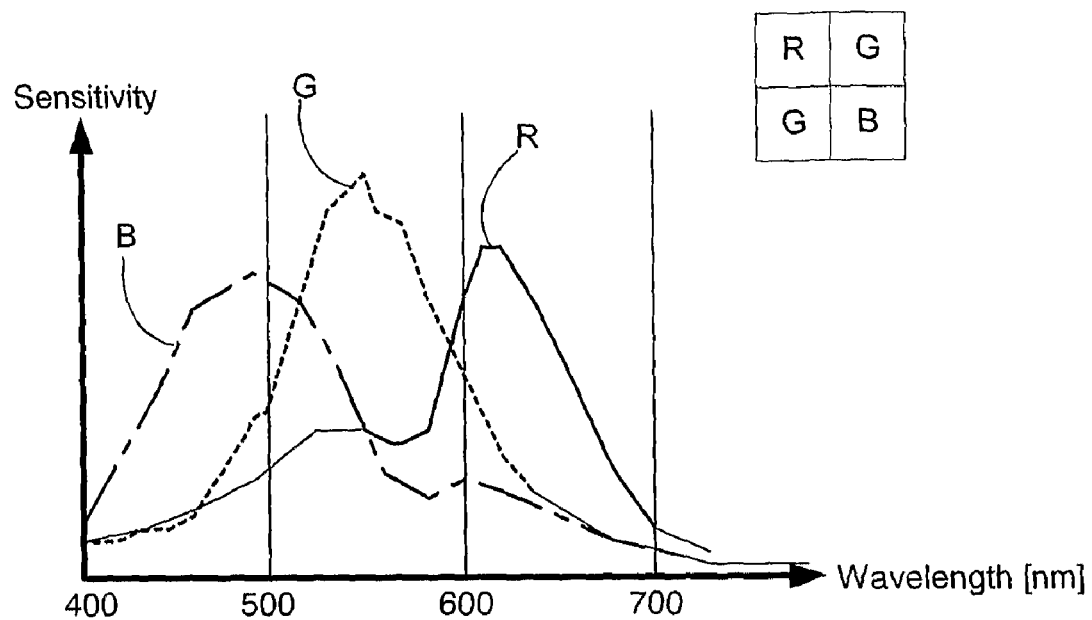
FIG. 1 is a graph of the normalized spectral response of a color camera module with a Bayer CFA.
Figure 2:
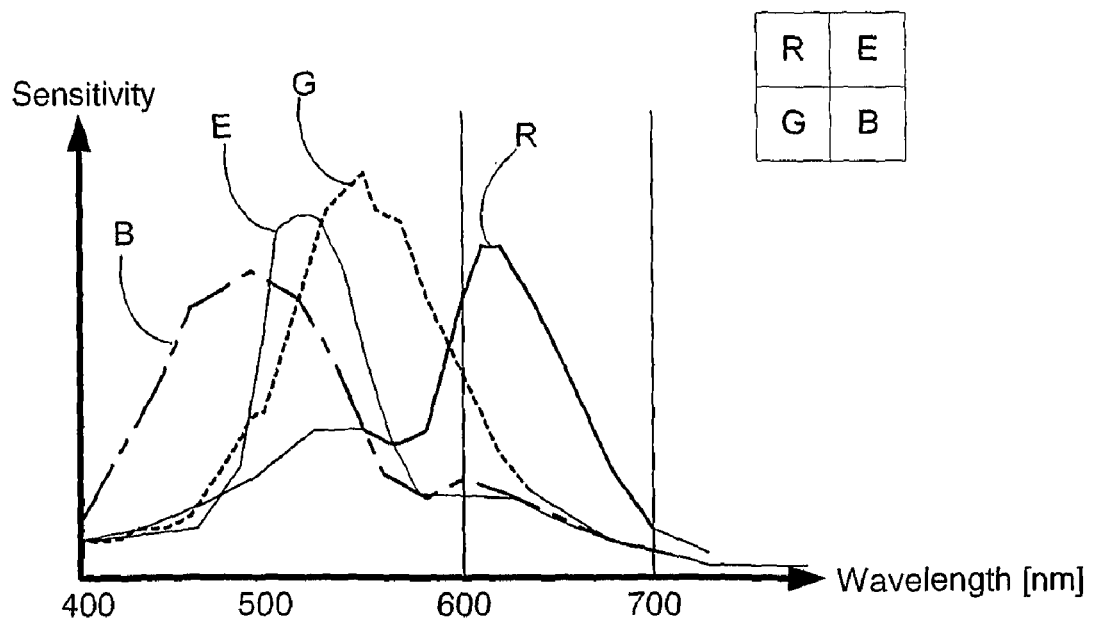
FIG. 2 is a graph of the normalized spectral response of a color camera module with a RGBE CFA.
Figure 3:
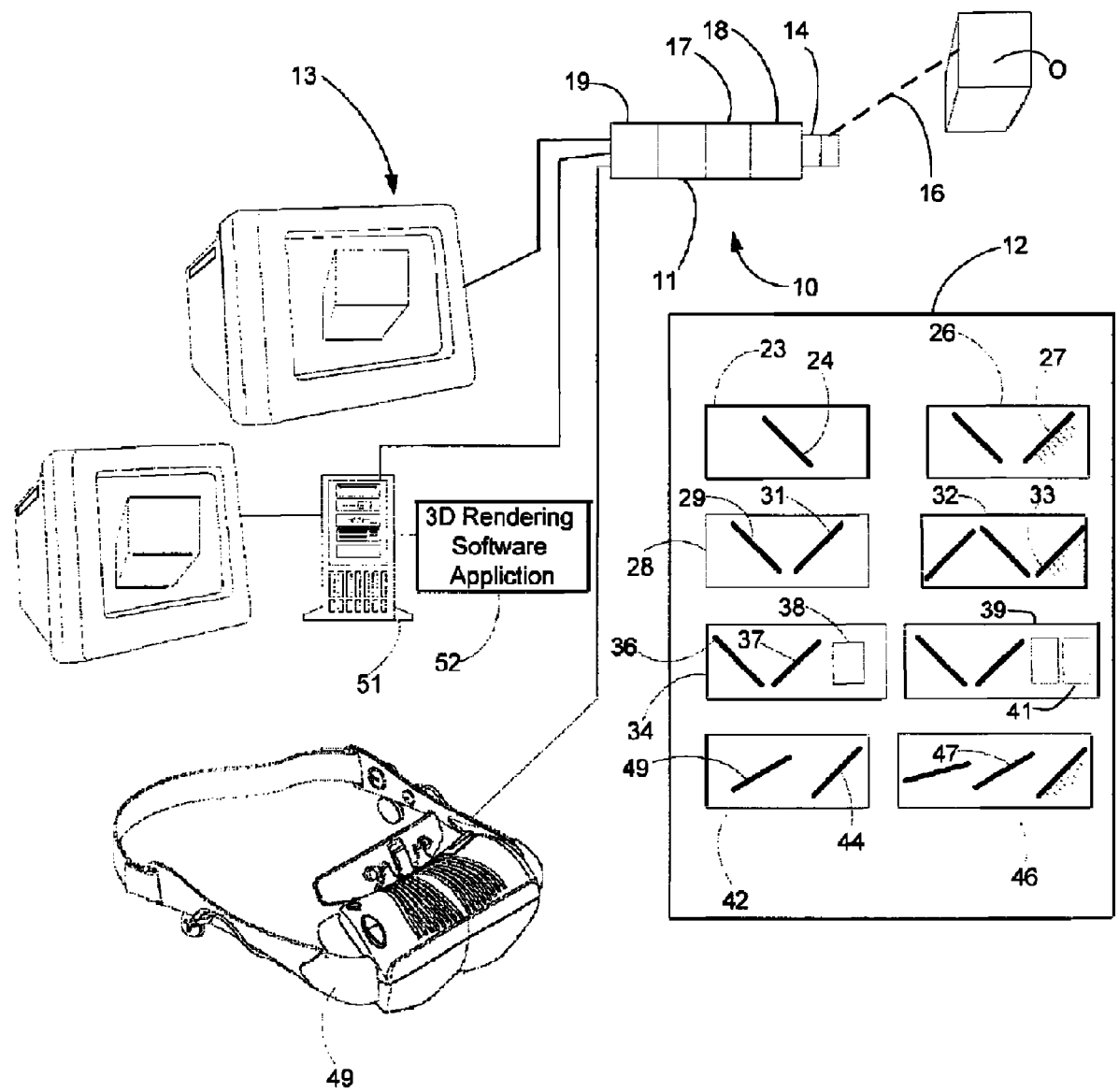
FIG. 3 is a schematic diagram of an image acquisition system including a Spectral Band Separation (SBS) module in accordance with the present invention.

FIG. 3 shows an image acquisition system 10 including a color camera module 11, an interchangeable Spectral Band Separation (SBS) module 12, and a display system 13. The image acquisition system 10 can be intended for 2D imaging applications including inter alia multiple 2D images, Extended Field Of View (EFOV) images, and the like, and 3D imaging applications including inter alia stereoscopic imaging, 3D rendering, and the like.

Figure 4:
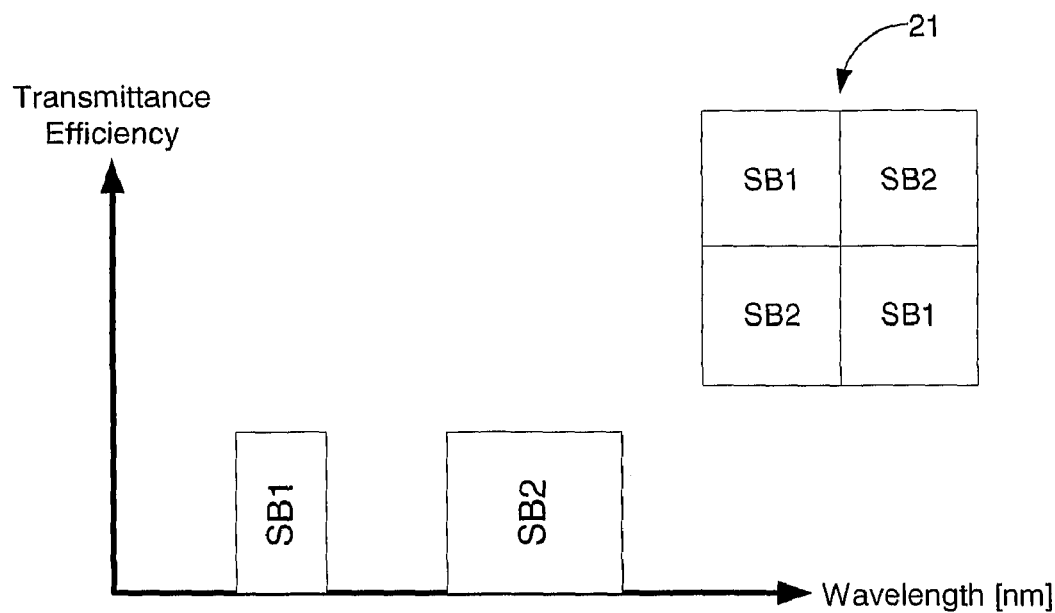
FIG. 4 is a graph of the normalized spectral response of a color camera module with a two color non overlap spectral band (2C NOSB) CFA in accordance with the present invention.
Figure 5:
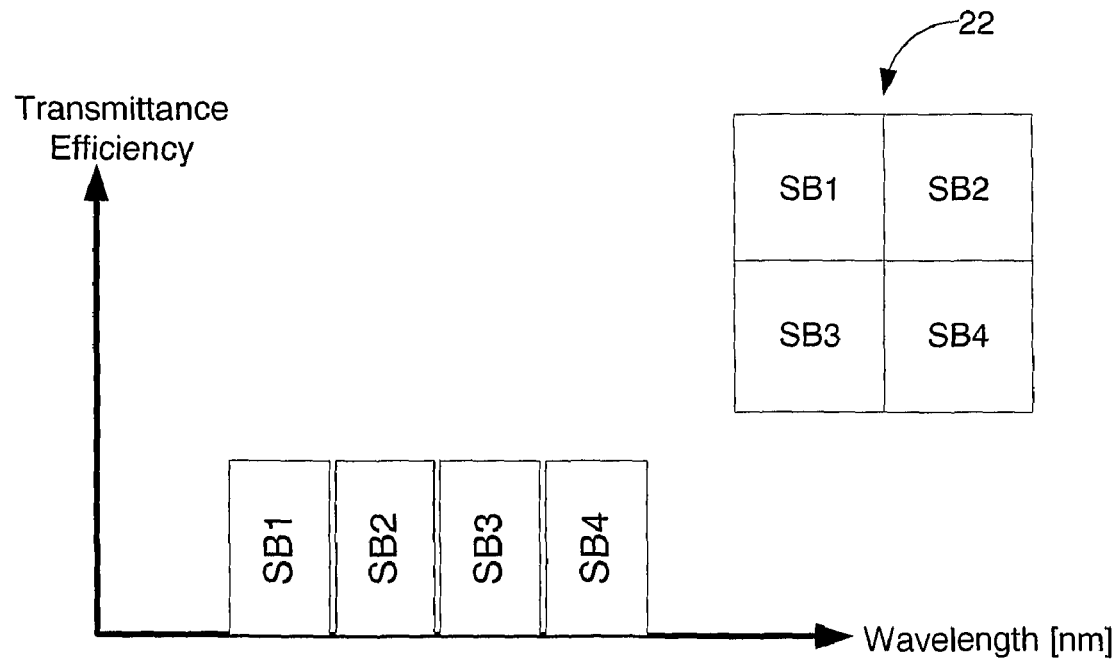
FIG. 5 is a graph of the normalized spectral response of a color camera module with a four color non overlap spectral band (4C NOSB) CFA in accordance with the present invention.

The color camera module 11 has imaging optics 14 with an optical axis 16, an image sensor 17 with a Color Filter Array (CFA) 18 and an output interface 19 with analog and/or digital outputs for transmitting still or live video signals to the display system 13. The imaging optics 14 may have a short depth of focus of a few mm or be telecentric typically having a depth of focus of a few cm depending on the application at hand. Telecentric imaging optics has the additional advantage that it precludes the need for an optical disk in the case of 3D imaging of objects at different object distances. The color camera module 11 can be a commercially available unit as aforementioned hereinabove or alternatively it can have non overlap spectral band CFAs. FIGS. 4 and 5 are graphs of the normalized spectral responses of color camera modules 21 and 22 with a two color non overlap spectral band (2C NOSB) color CFA and a four color non overlap spectral band (4C NOSB) color CFA, respectively. The spectral bands can be within the 400-700 nm visual spectral band only, or the >700 nm IR spectral band only, or the <400 nm UV spectral band only, or a combination of the visual, IR and UV spectral bands depending on the application at hand.

SBS modules 12 each include at least one dichroic element and optionally a mirror furthermost from the color camera module 11 for imaging along a line of sight transversing an imaging optics' optical axis 16. SBS modules 12 dedicated for 2D imaging applications include: SBS module 23 with a single dichroic element 24. SBS module 26 is similar to SBS module 23 but with an additional furthermost mirror 27. SBS module 28 has a proximate dichroic element 29 and a distal dichroic element 31. SBS module 32 is similar to SBS module 28 but with an additional furthermost mirror 33. SBS module 34 has a proximate dichroic element 36, an intermediate dichroic element 37, and a distal dichroic element 38. SBS module 39 is similar to the SBS module 34 but with an additional furthermost mirror 41. SBS modules 12 dedicated for 3D imaging applications include a 3D SBS module 42 with a single dichroic element 43 and a furthermost mirror 44, and a 3D SBS module 46 similar to the SBS module 42 but with an additional dichroic element 47 between the dichroic element 43 and the furthermost mirror 44.

The display system 13 can be implemented by one or more monitors 48, head mounted 2D or 3D goggles 49, computers 51 running 3D rendering software applications 52 for 3D rendering of an object, and the like. Exemplary 3D goggles include inter alia Model No. DH-4400 3D Model commercially available from CyberMind Interactive Nederland, Rijksweg 74a-6228 XZ Maastricht, The Netherlands (www.cybermind.nl). Exemplary 3D rendering software applications include inter alia Imageware commercially available from ImageWare Systems, Inc., USA, and from Deep Exploration commercially available from Right Hemisphere, Inc., USA, and the like.

2D Imaging Applications

Figure 6:
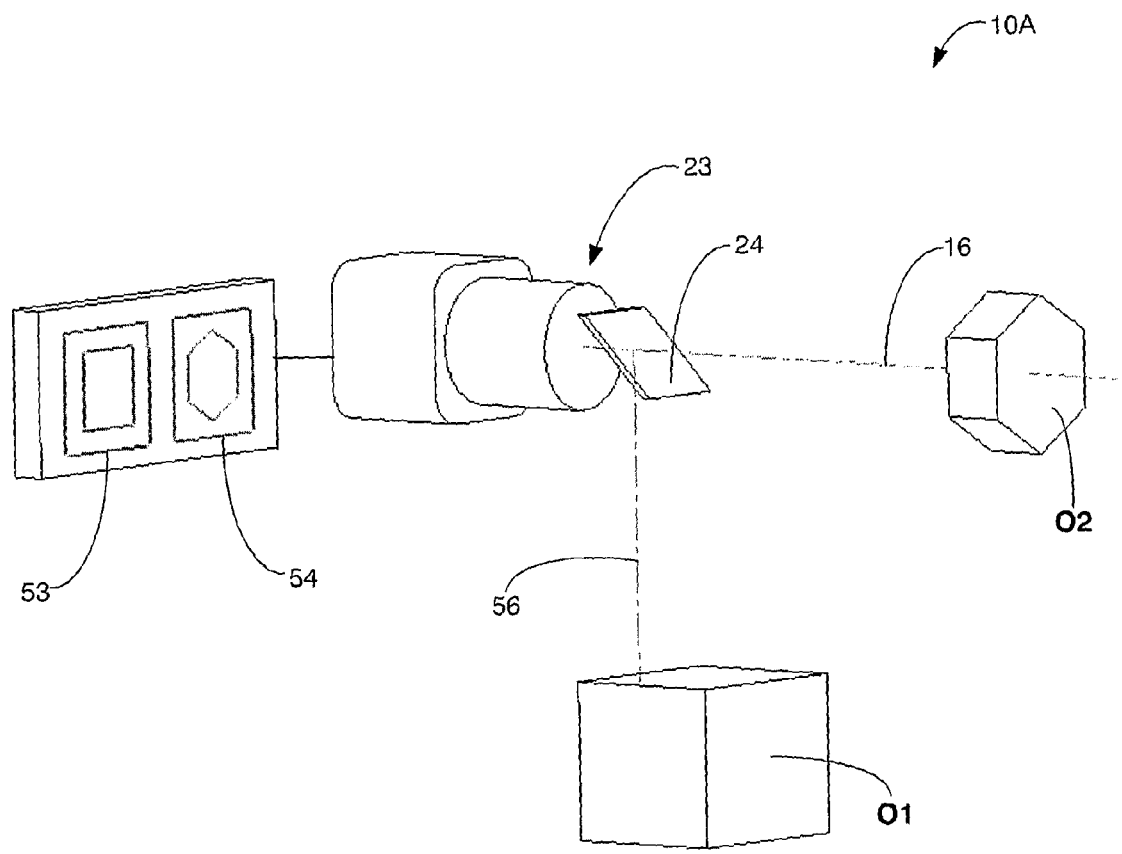
FIG. 6 is an optical setup of an image acquisition system including an SBS module for displaying two different 2D images, and a table listing spectral responses of the SBS module suitable for different CFAs.

FIG. 6 shows an image acquisition system 10A including the SBS module 23 with the dichroic element 24 for imaging two objects O1 and O2 on a pair of monitors 53 and 54, respectively, or viewing by way of 2D goggles 49. The SBS module 23 can be adapted for use with any one of a Bayer CFA, an RGBE CFA, a 2C NOSB CFA, and a 4C NOSB CFA. The dichroic element 24 has a reflected field of view $FOV_R$ corresponding to its reflected spectral band R1 for imaging the object O1 along a line of sight 56 transverse to the optical axis 16 on the monitor 53, and a transmitted field of view $FOV_T$ corresponding to its transmitted spectral band T1 for imaging the object O2 along a line of sight 57 co-directional with the optical axis 16 on the monitor 54, respectively.

Figure 7:
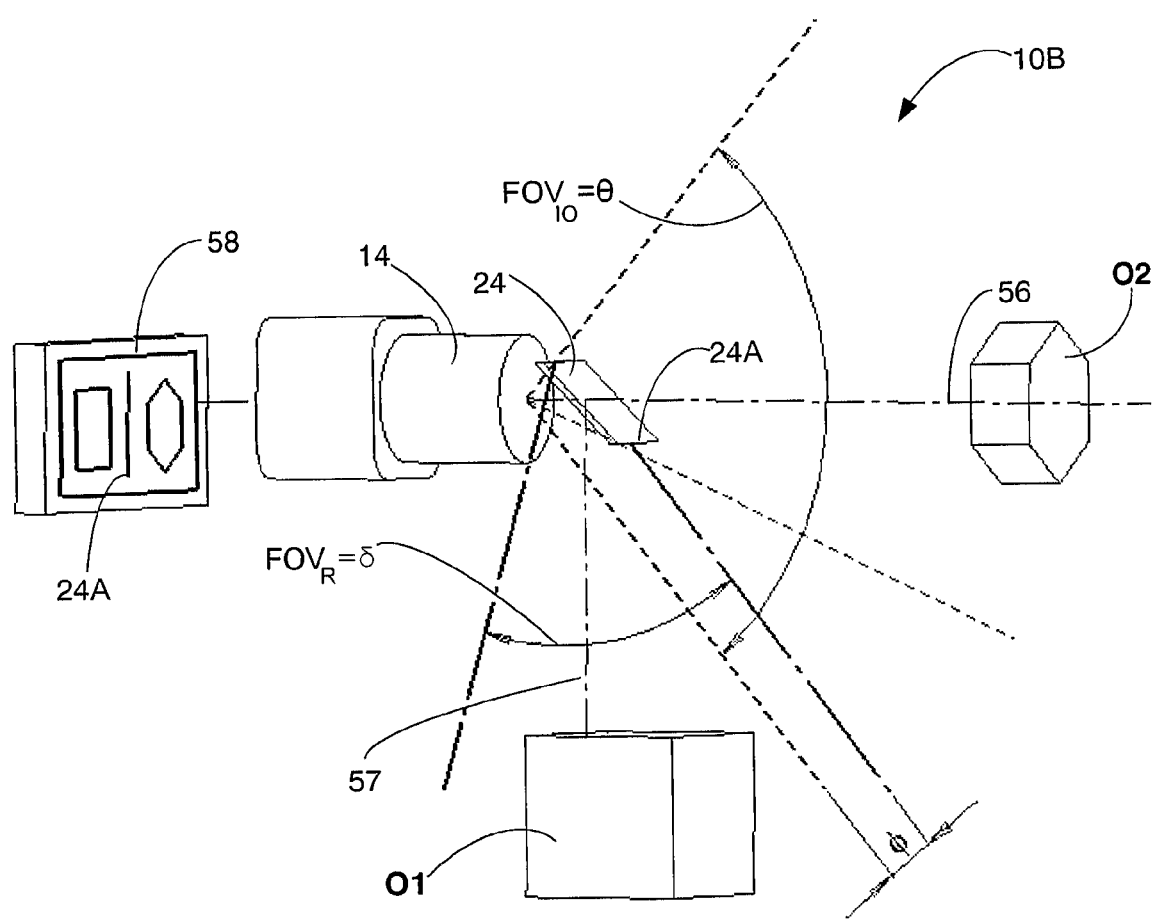
FIG. 7 is an optical setup of an image acquisition system for displaying Extended Field Of View (EFOV) images.

FIG. 7 shows an image acquisition system 10D similar to the image acquisition system 10A, but with an imaging optics 14 having a nominal field of view $FOV_{IO}$ such that its dichroic element's reflected field of view $FOV_R$ overlaps the $FOV_{IO}$ by, say, $\phi=15°$ to render an extended field of view (EFOV) image including images of both objects O1 and O2 for display on a single monitor 58. The EFOV image has a field of view $\theta+\delta-\phi$ where $\theta$ is the imaging optics' nominal field of view $FOV_{IO}$ and $\delta$ is the dichroic element's reflected field of view $FOV_R$ and is necessarily edited to delete the overlap between the $FOV_{IO}$ and the $FOV_R$ including inter alia the image of the dichroic element's edge 24A at the grazing incidence of the imaging optics 14.

Figure 8:
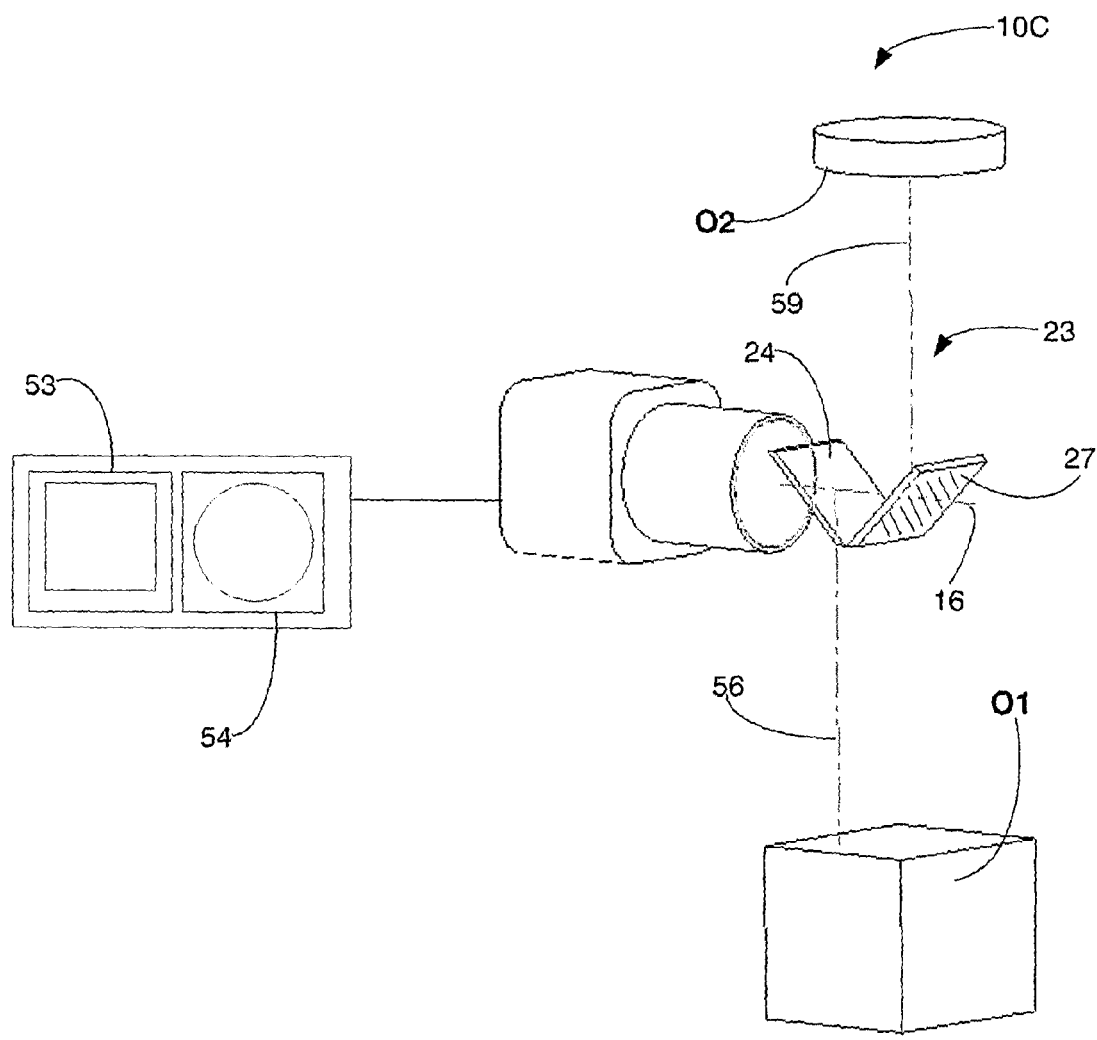
FIG. 8 is an optical setup of an image acquisition system including an alternative SBS module for displaying two different 2D images.

FIG. 8 show an image acquisition system 10C similar to the image acquisition system 10A and differing therefrom insofar that it includes the SBS module 26 with the dichroic element 24 and the mirror 27 for imaging along a line of sight transversing the optical axis 16. The SBS module 26 is operative with the same CFAs as the SBS module 23. The dichroic element 24 has a reflected field of view $FOV_R$ corresponding to its reflected spectral band R1 for imaging the object O1 along the line of sight 56 transverse to the optical axis 16 on the monitor 53, and a transmitted field of view $FOV_T$ corresponding to its transmitted spectral band T1 for imaging the object O2 along a line of sight 59 also transverse to the optical axis 16 via the mirror 27 on the monitor 54, respectively. Alternatively, the image acquisition system 10C can image the two objects on a single EFOV image in a similar manner as the image acquisition system 10B.

Figure 9:
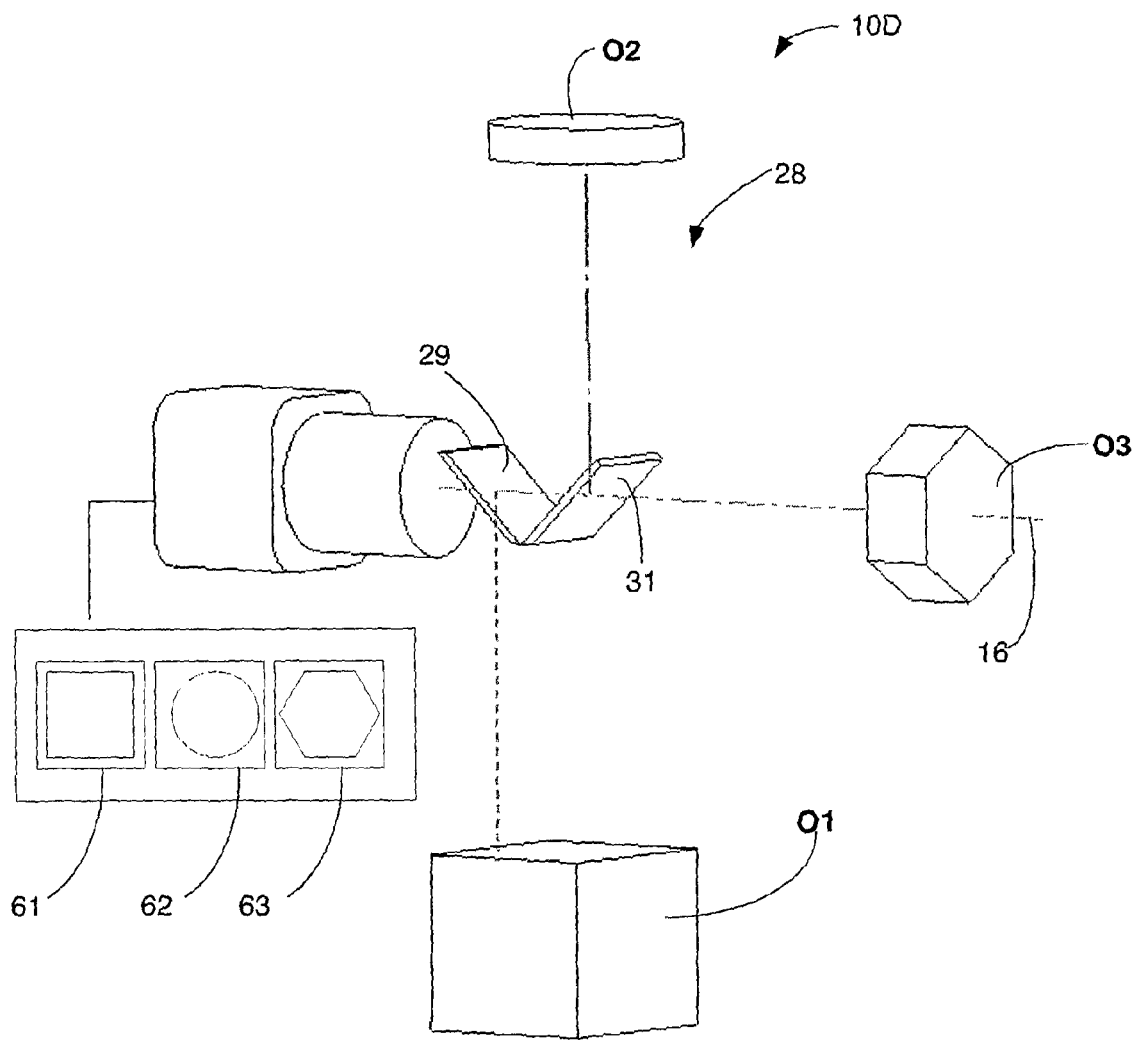
FIG. 9 is an optical setup of an image acquisition system including an SBS module for displaying three different 2D images, and a table listing spectral responses of the SBS module suitable for different CFAs.

FIG. 9 shows an image acquisition system 10D similar to the image acquisition system 10A and differing therefrom insofar it includes the SBS module 28 for imaging three objects O1, O2, and O3 on a plane including the optical axis 16 on monitors 61, 62, and 63, respectively. Alternatively, the image acquisition system 10D can image the three objects on a single EFOV image in a similar manner as the image acquisition system 10B. The SBS module 28 can be adapted for use with any one of a Bayer CFA, an RGBE CFA, and a 4C NOSB CFA.

Figure 10:
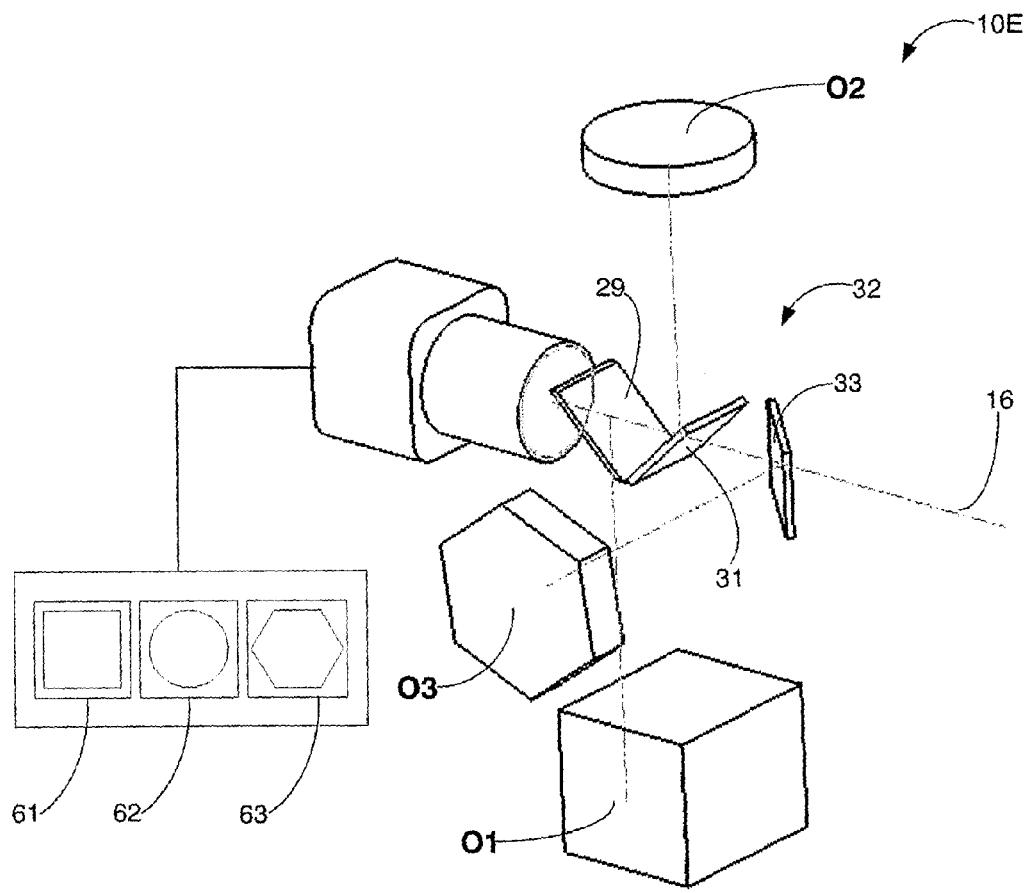
FIG. 10 is an optical setup of an image acquisition system including an alternative SBS module for displaying three different 2D images, and a table listing spectral responses of the SBS module suitable for different CFAs.

FIG. 10 shows an image acquisition system 10E similar to the image acquisition system 10D and differing therefrom insofar it includes the SBS module 32 with the mirror 33 for imaging three objects O1, O2 and O3 on a plane transverse to the optical axis 16. Alternatively, the image acquisition system 10E can image the three objects on a single EFOV image in a similar manner as the image acquisition system 10B. The SBS module 32 can be adapted for use with the same CFAs as the SBS module 28.

Figure 11:
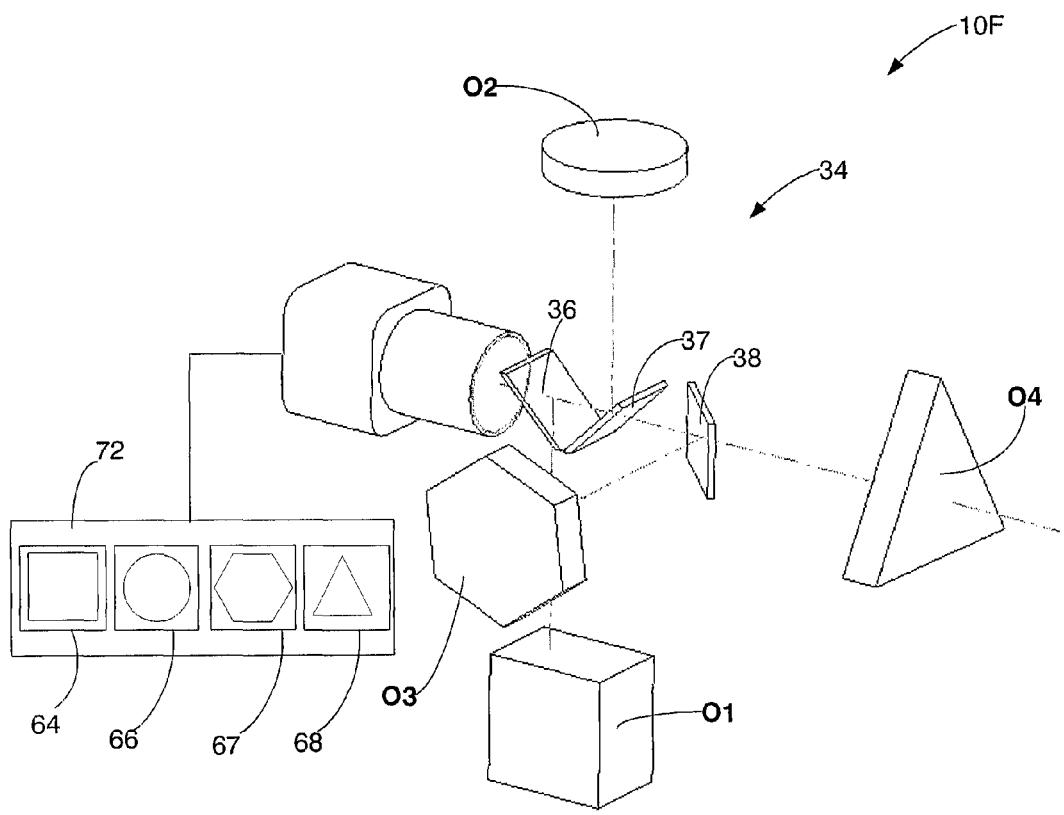
FIG. 11 is an optical setup of an image acquisition system including an SBS module for displaying four different 2D images, and a table listing the spectral response of the SBS module for different CFAs.

FIG. 11 shows an image acquisition system 10F similar to the image acquisition system 10A and differing therefrom insofar it includes the SBS module 34 for imaging four objects O1, O2, O3, and O4 on monitors 64, 66, 67 and 68, respectively. The SBS module 34 can be adapted for use with either an RGBE CFA or a 4C NOSB CFA. Alternatively, the image acquisition system 10F can image two objects O1 and O2 on a single EFOV image in a plane transverse to the optical axis 16 and two objects O3 and O4 on a single EFOV image in a plane including the optical axis 16. Alternatively, other EFOV images with two or three objects can be imaged.

Figure 12:
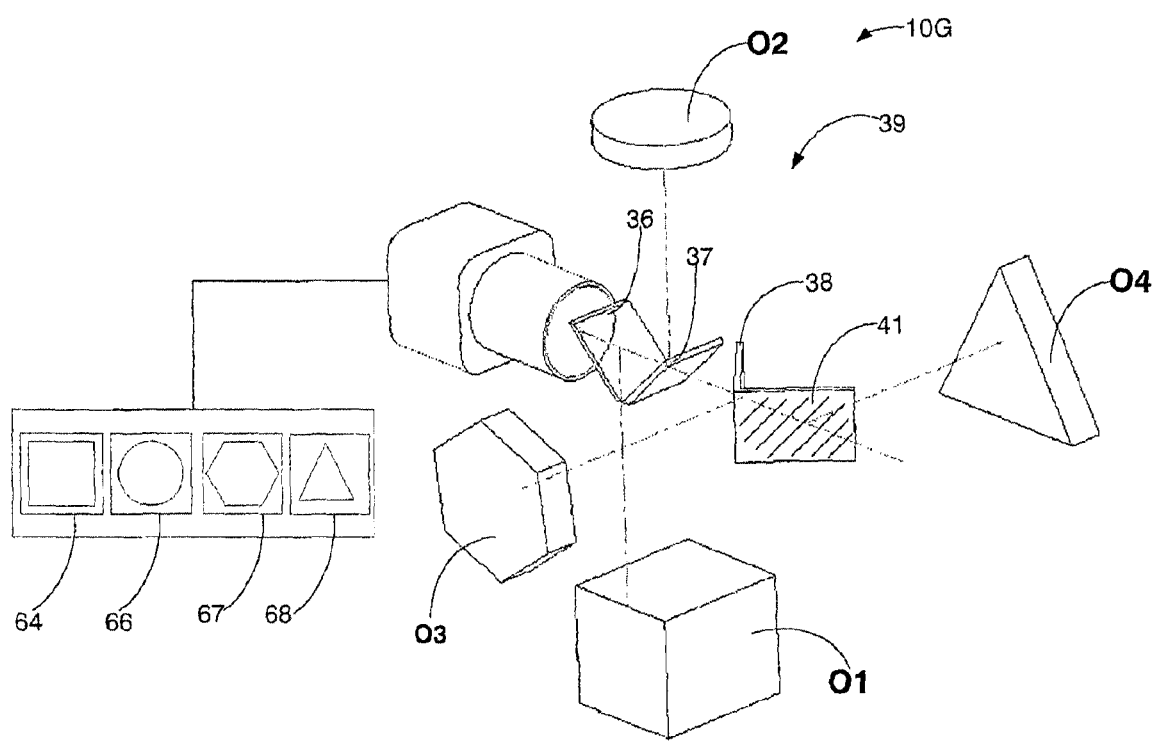
FIG. 12 is an optical setup of an image acquisition system including an alternative SBS module for displaying four different 2D images.

FIG. 12 shows an image acquisition system 10G similar to the image acquisition system 10F and differing therefrom insofar it includes the SBS module 39 with the mirror 41 for imaging along a line of sight traversing the optical axis 16. Alternatively, the image acquisition system 10G can image the four objects on a single 360° EFOV image in a similar manner as the image acquisition system 10B. The SBS module 39 can be adapted for use with the same CFAs as the SBS module 34.

Figure 13:
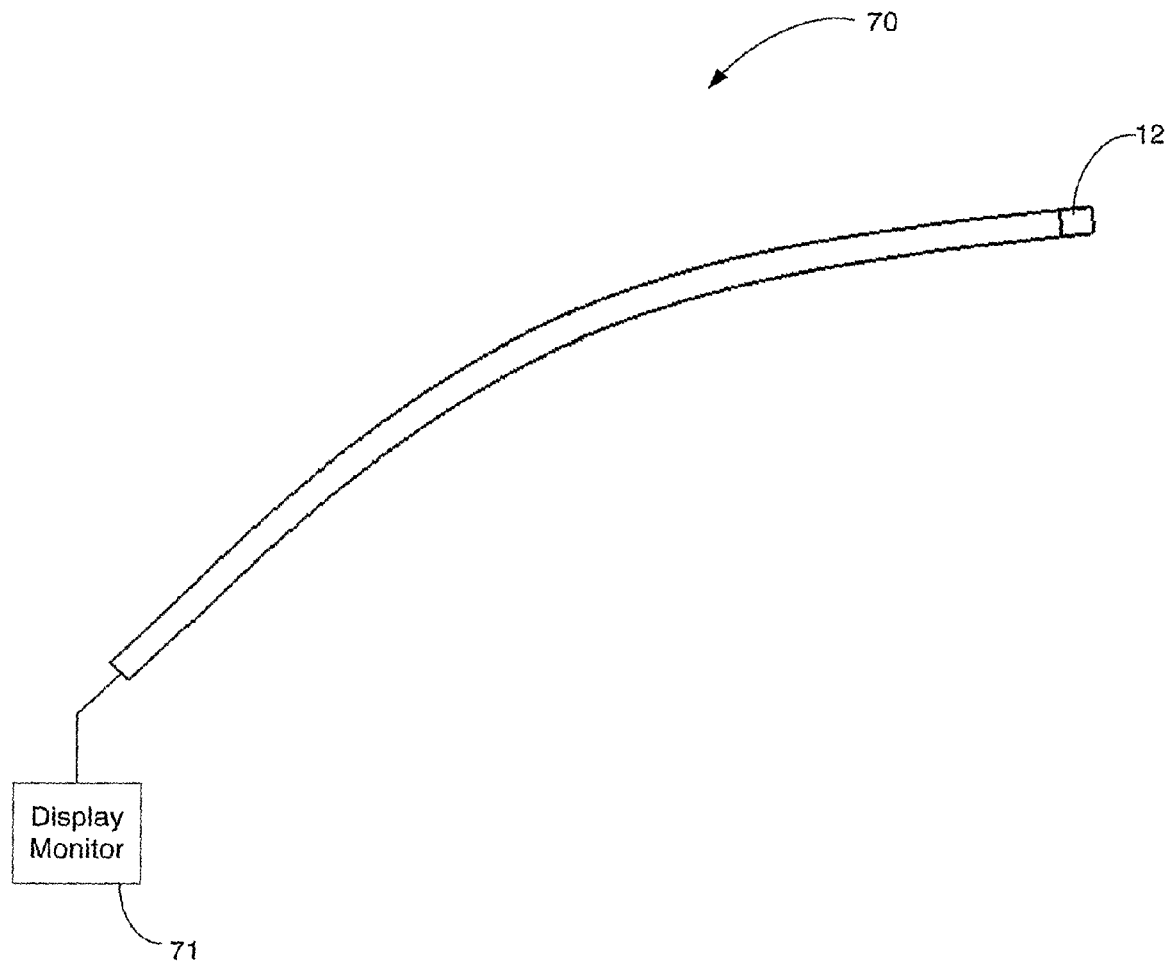
FIG. 13 is a schematic diagram of an endoscope including an SBS module in accordance with the present invention.
Figure 14:
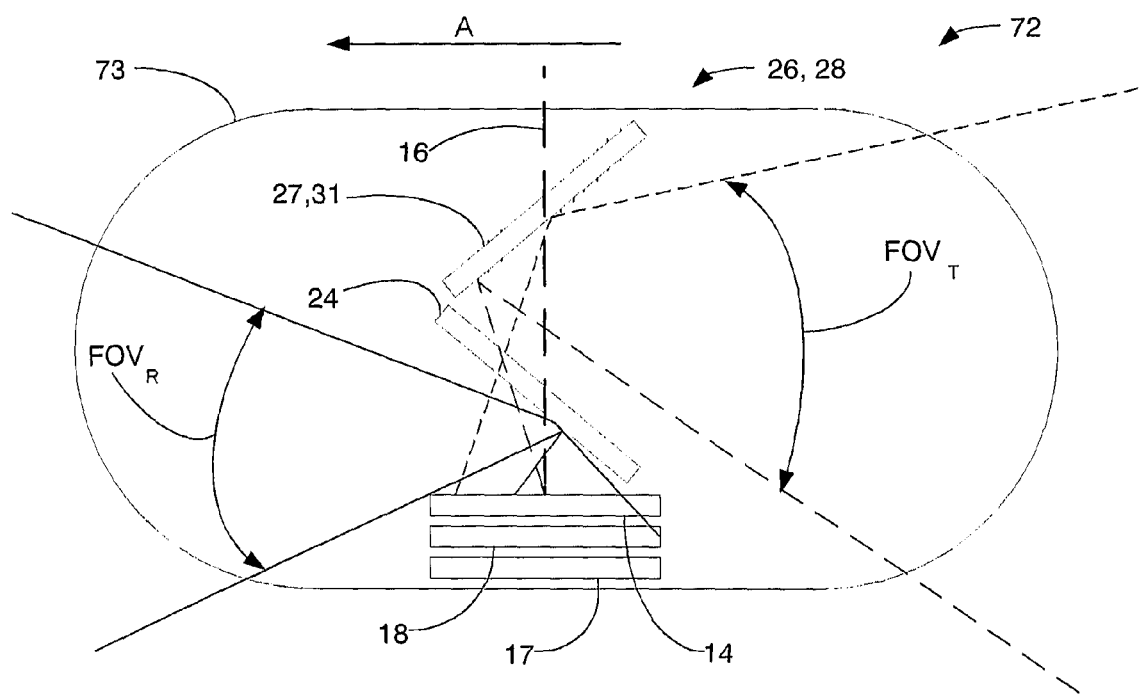
FIG. 14 is a schematic diagram of an endoscope capsule including an SBS module in accordance with the present invention.

FIG. 13 shows an endoscope 70 including an SBS module 12 for imaging clinical images on a display monitor 71 for diagnostic purposes. Suitable SBS modules 12 include all the 2D modules. FIG. 14 shows an endoscope capsule 72 having an ellipsoid shaped transparent housing 73 intended for travel along a direction of travel denoted A co-directional with its major axis. The endoscope capsule 72 accommodates imaging optics 14, an image sensor 17 and a SBS module 26 or 28 arranged for imaging both forward and rearward with respect to its intended direction of travel A.

3D Imaging Applications

Figure 15:
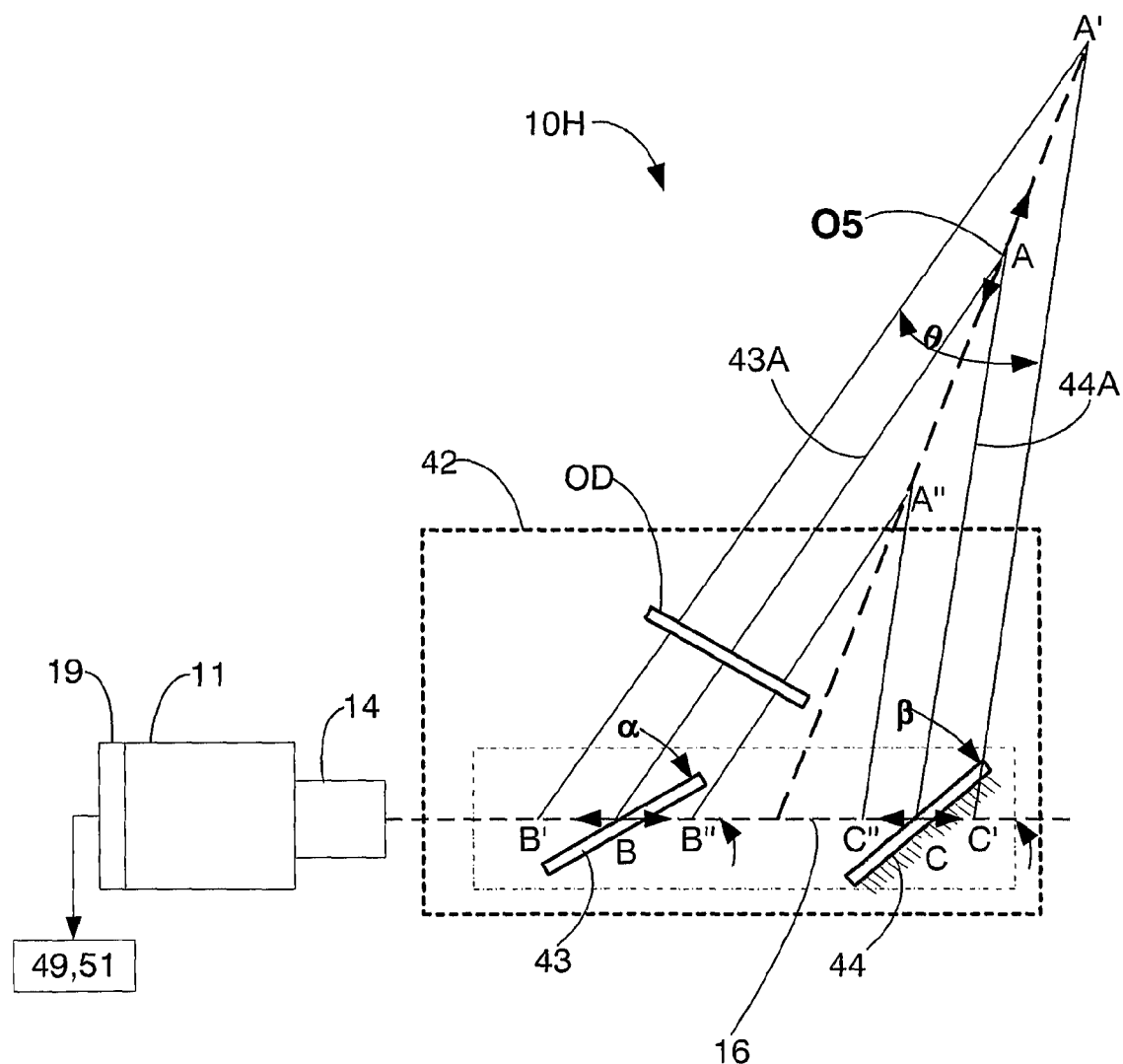
FIG. 15 is an optical setup of an image acquisition system for stereoscopic imaging of an object.

FIG. 15 shows an image acquisition system 10H for use either 3D goggles 49 or the 3D rendering software application 52. The image acquisition system 10H includes a color camera module 11 with imaging optics 14 having an optical axis 16, and the SBS module 42 with the proximate dichroic element 43 and the distal mirror 44 relative to the imaging optics 14. The dichroic element 43 and the mirror 44 have lines of sight 43A and 44A intercepting at an object O5 at a nominal object position A. The SBS module 42 can preferably image the object O5 over a variable object distance between extreme object positions A' and A". The lines of sight subtend acute angles $\alpha$ and $\beta$ with respect to the optical axis 16, and an acute angle $\theta$ preferably in the range of $10°<\theta<20°$ where $\beta=\alpha+\frac{1}{2}\theta$. The SBS module 42 preferably has a symmetrical arrangement in which $\alpha+\beta=90°$ excluding the singular arrangement $\alpha=\beta$. The SBS module 42 can be adapted for use with the same CFAs as the SBS module 23. The output interface 19 transmits signals corresponding to the images of the reflected spectral band R1 from the dichroic element 43 and the transmitted spectral band T1 reflected by the mirror 44.

A variable focus SBS module 42 is preferably achieved by enabling sliding displacement of the dichroic element 43 and the mirror 44 in opposite directions with respect to a nominal separation therebetween. Outward displacement of the dichroic element 43 and the mirror 44 with respect to their nominal positions for increasing the nominal separation therebetween provides for larger object distances, namely, object distances A'. Conversely, inward displacement of the dichroic element 43 and the mirror 44 with respect to their nominal positions for decreasing the nominal separation therebetween provides for smaller object distances, namely, A". Alternatively, one of the dichroic element 43 and the mirror 44 may be fixedly mounted and the other slidingly displaceable with respect thereto in which case the object O would necessarily have to be deployed at a different position along the optical axis 16.

In the case that the imaging optics 14 is not telecentric, the SBS module 42 preferably includes an optical disk OD for compensating for the fact that the object distance from the imaging optics 14 to the object O5 is shorter via the dichroic element 43 than via the mirror 44 by the separation BC therebetween, namely, the so-called Optical Path Difference (OPD). The thickness T of the optical disk OD is calculated according to the relationship T=OPD/n where n is the refractive index of the optical disk. For example, if the OPD=10 mm, and the refractive index n=1.8, then the optical disk OD has a thickness T=5.5 mm.

The image acquisition system 10H can be alternatively implemented by a SBS module with a second dichroic element instead of the mirror 44 in which case the output interface 19 transmits signals corresponding to the images of the two reflected spectral bands.

Figure 16:
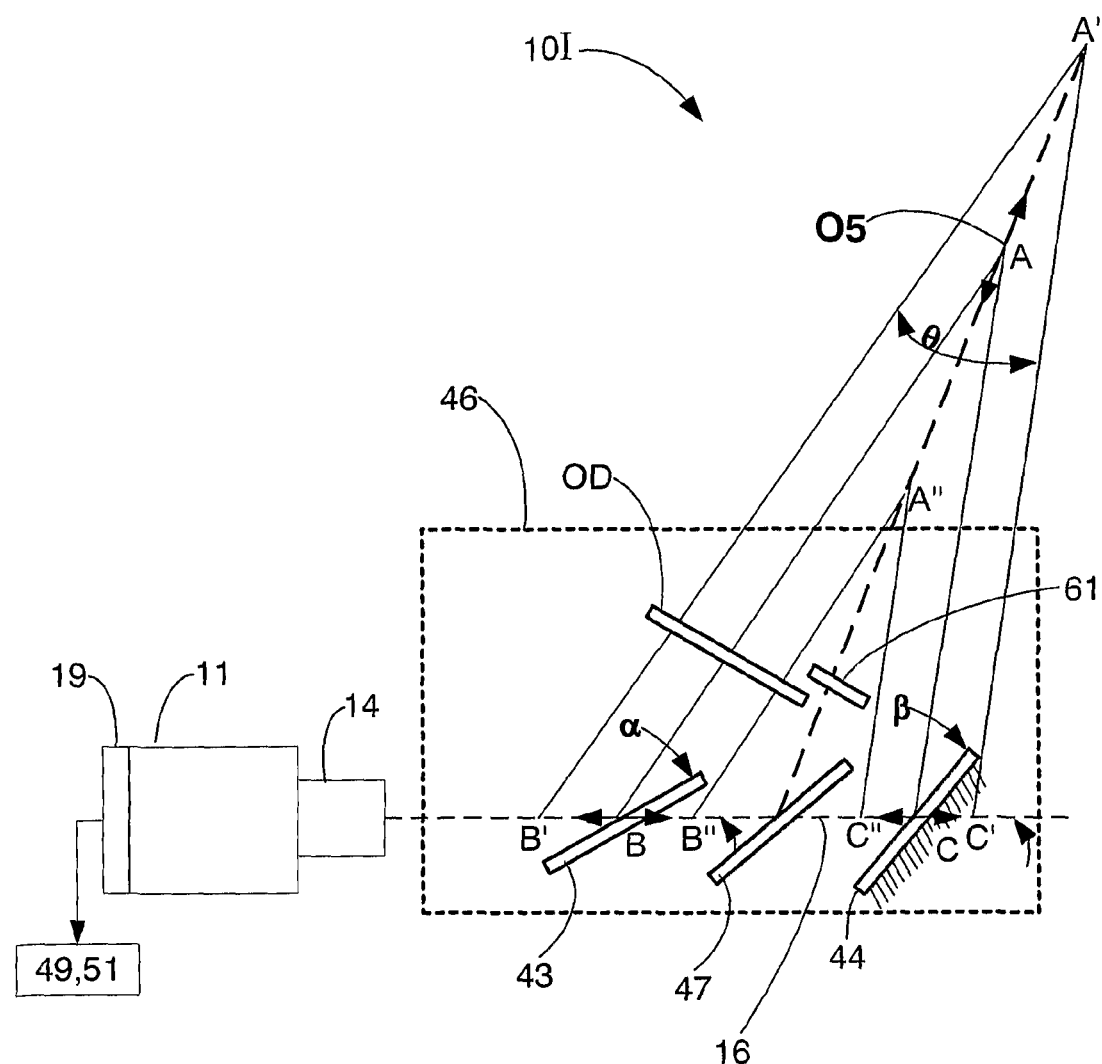
FIG. 16 is an optical setup of an image acquisition system for 3D rendering of an object.

FIG. 16 shows an image acquisition system 10I similar to the image acquisition system 10H, except that it includes an additional dichroic element 47 intermediate the dichroic element 43 and the mirror 44 for improved image correlation.

While the invention has been described with respect to a limited number of embodiments, it will be appreciated that many variations, modifications, and other applications of the invention can be made within the scope of the appended claims.

The invention claimed is:

1. A Spectral Band Separation (SBS) module for use with a color camera module having imaging optics with an optical axis, and an image sensor with a color filter array for filtering incoming radiation into at least two different spectral bands for 3 dimensional imaging of an object, the SBS module comprising
at least one dichroic element and a mirror disposed along the optical axis, said at least one dichroic element being disposed closer to the color camera module with respect to said mirror,
said at least one dichroic element and said mirror obliquely intercepting the optical axis and having lines of sight intercepting at the object for imaging at least two different images along non co-directional lines of sight on the image sensor to enable the generation of a 3D image of the object.

2. The module according to claim 1 wherein said dichroic element and said mirror have a variable separation therebetween for imaging objects over a range of object distances.

3. The module according to claim 1 wherein said at least one dichroic element includes a first dichroic element proximate the image sensor and a second dichroic element remote therefrom wherein said first dichroic element transmits radiation reflected by said second dichroic element.

4. The module according to claim 3 wherein said first dichroic element and said second dichroic element have lines of sight intercepting at the object for imaging the object.

5. The module according to claim 4 wherein said first dichroic element and said second dichroic element have a variable separation therebetween.

6. A color camera module comprising:
(a) imaging optics with an optical axis;
(b) an image sensor with a color filter array for filtering incoming radiation into at least two different spectral bands; and
(c) a Spectral Band Separation (SBS) module according to claim 1.

7. The module according to claim 6 wherein said color filter array filters incoming radiation into non-overlapping spectral bands.

8. The module according to claim 7 wherein said non-overlapping spectral bands have equal bandwidths.

9. An image acquisition system comprising:
(a) a color camera module having imaging optics with an optical axis, and an image sensor with a color filter array for filtering incoming radiation into at least two different spectral bands; and
(b) a Spectral Band Separation (SBS) module according to claim 1.

10. The system according to claim 9 wherein said color filter array filters incoming radiation into non-overlapping spectral bands.

11. The system according to claim 10 wherein said non-overlapping spectral bands have equal bandwidths.

12. An endoscope comprising a SBS module according to claim 1.

13. The endoscope according to claim 12 implemented as a capsule intended for Swallowing.

* * * * *